United States Patent
Hsung et al.

[11] Patent Number: 5,913,878
[45] Date of Patent: Jun. 22, 1999

[54] TIERED THERAPY CARDIAC DETECTION SYSTEM HAVING A GLOBAL COUNTER

[75] Inventors: Jean-Cheui Hsung, Shoreview; Mark Stockburger, Inver Grove Heights, both of Minn.

[73] Assignee: Angeion Corporation, Minneapolis, Minn.

[21] Appl. No.: 09/021,650

[22] Filed: Feb. 10, 1998

[51] Int. Cl.$^6$ ........................................ A61N 1/39
[52] U.S. Cl. ................................................ 607/5
[58] Field of Search ........................................ 607/4, 5, 6

[56] References Cited

U.S. PATENT DOCUMENTS

| | | |
|---|---|---|
| 4,375,817 | 3/1983 | Engle et al. . |
| 4,830,006 | 5/1989 | Haluska et al. . |
| 4,971,058 | 11/1990 | Pless et al. . |
| 5,184,615 | 2/1993 | Happholz et al. . |
| 5,318,591 | 6/1994 | Causey, III et al. . |
| 5,403,355 | 4/1995 | Alt . |
| 5,458,620 | 10/1995 | Adams et al. . |
| 5,730,141 | 3/1998 | Fain et al. . |

Primary Examiner—William E. Kamm
Attorney, Agent, or Firm—Brad Pedersen

[57] ABSTRACT

A tiered therapy cardiac detection system is provided for a medical device that senses cardiac signals representative of beat-to-beat intervals and delivers at least one therapy in response to a detected cardiac dysrhythmia corresponding to one of a plurality of programmed zones of heart rates. The detection system includes a global counter that counts at least all beat-to-beat intervals indicating a rate greater than a programmed threshold value representative of a minimum heart rate for delivering any therapy once an initial threshold condition is met. A plurality of window memories and parameter memories are provided in the device. Each window memory corresponds to a given one of the zones and stores an indication of whether each of a last N cardiac signals are within that zone. Each parameter memory corresponds to a given one of the zones and stores a programmed trigger value of the global counter required in order for a therapy in that zone to be delivered. Processing circuitry evaluates the global counter, the window memories and the parameter memories on a beat-by-beat basis and indicates that a cardiac dysrhythmia has been detected for a given zone if the global counter exceeds the programmed trigger value for that zone and the indications stored by the window memory for that zone satisfy a predetermined criteria.

26 Claims, 9 Drawing Sheets

Fig. 8

```
                1 2 3 4 5 6 7 8 9 10
                    ****  *****              DURATION 10
TRL  |_____ 200 BPM
     |          *
     |     000000000000000                   DURATION 15
MRL  |_ _ _ _ _ _ _ _ _ _ _ _ _ _ _ _ _ _ _ _ _ _  150 BPM
     |
     |     XXXXXXXXXXXXXXXXXXX                DURATION 20
PRL  |_____ 120 BPM
         000
         ***
         XXX
```

Fig. 9

```
                1 2 3 4  5  6 7 8 9 10
                           *****             DURATION 10
TRL  |_____ 200 BPM
     |                *
     |          ****                         DURATION 15
MRL  |_ _ _ _ _ _ _ _ _ _ _ _ _ _ _ _ _ _ _ _ _ _  150 BPM
     |
     |                                       DURATION 20
PRL  |_____ 120 BPM
              ***
```

Fig. 10

```
     |
     |                                       DURATION 10
TRL  |_____ 200 BPM
     |
     |                                       DURATION 15
MRL  |_ _ _ _ _ _ _ _ _ _ _ _ _ _ _ _ _ _ _ _ _ _  150 BPM
     |        1 2 3 4 5 6   7 8 9
     |        *****   ***                    DURATION 20
PRL  |_____ 120 BPM
                **          ***
          •  **      1 2    1 2 3
```

Fig. 11

```
            1 2 3 4 5 6 7 8 9 10 11 12 13
TRL    |                                              DURATION 10        200 BPM
       |                    *
       |    ***    ***    * * *    (ATP) Shk1Shk2Shk³                    150 BPM
MRL    |- - - - - - - - - - - - - - - - - - - - - - - - - - - - - - - -
       |      0 0      0 0
PRL    |                                                                 120 BPM
```

Fig. 12

```
            1 2 3 4 5 6 7 8 9 10 11 12 13 14 15 16 17 18 19
                        *                     t
                                                          DURATION 10
TRL    |          *           *     *                                    200 BPM
       |              * *        * *      m m m
       |         * * *                                    DURATION 15
MRL    |- - - - - - - - - - - - - - - - - - - - - - - - - - - - - - - -  150 BPM
       |         * * * *                                  DURATION 15
PRL    |                                                                 120 BPM
```

Fig. 13

```
            1 2 3 4 5 6 7 8 9 10 11 12 13 14 15 16 17 18 19
              t t                                DURATION 10
TRL    |           t  t         t  t                                     200 BPM
       |           mm      mm      m
       |       ***                   m          DURATION 15
MRL    |- - - - - - - - - - - - - - - - - - - - - - - - - - - - - - - -  150 BPM
       |       ***            p                 DURATION 15
PRL    |                                                                 120 BPM
```

TIERED THERAPY CARDIAC DETECTION SYSTEM HAVING A GLOBAL COUNTER

FIELD OF THE INVENTION

The present invention relates to medical devices for treating cardiac dysrhythmias such as anti-tachycardia pacemakers and implantable cardioverter defibrillator (ICD) devices. More particularly, the present invention pertains to a tiered therapy cardiac detection system that utilizes a global counter to detect cardiac dysrhythmias for heart rates in different programmable zones, each zone being associated with a different tiered therapy.

BACKGROUND OF THE INVENTION

Medical devices for treating cardiac dysrhythiams, such as anti-tachycardia pacemakers and implantable cardioverter defibrillator (ICD) devices are well known. Almost all current ICD devices utilize cardiac detection systems which monitor the heart beat and detect cardiac dysrhythmias based on a tiered therapy concept. Tiered therapy is simply the delivery of a different therapy depending upon how fast the heart is beating when a cardiac dysrhythmia is detected. A tiered therapy cardiac detection system monitors for heart rates that fall in one of several different programmable therapy zones. Each therapy zone is associated with a different tiered therapy to be delivered in response to detection of a cardiac dysrhythmia in that zone. For example, a heart rate in the range of 160 to 200 beats per minute might be classified as indicative of a ventricular tachycardia, in which case the preferred therapy might be anti-tachycardia pacing; whereas a heart rate over more than 240 beats per minute might be indicative of a ventricular fibrillation, in which case the preferred therapy might be delivery of a high voltage defibrillation countershock. A more detailed explanation and comparison of the tiered therapy detection systems of three existing ICD systems (the Medtronic Jewel®, the Ventritex Cadence® and the CPI Ventak® PRx®) can be found in Olson et al., "Properties and Performance of Rate Detection Algorithms in Three Implantable Cardioverter-Defibrillators", *IEEE Computers in Cardiology*, 0276-6547:65-68 (1994); and Anderson et al., "Performance of Basic Ventricular Tachycardia Detection Algorithms in Implantable Cardioverter Defibrillators", PACE, Vol. 20, Dec. 1997, pp. 2975-2983. Examples of tiered therapy cardiac detection systems can also be found in U.S. Pat. Nos. 4,375,817, 4,830,006, 4,971,058, 5,184,615, 5,318,591, 5,403,355, and 5,458,620.

The advantage of tiered therapy cardiac detection systems over other types of cardiac detection systems is that a tiered therapy cardiac detection system provides for flexibility without undue complexity in terms of how a physician can program the device. While tiered therapy detection systems are preferred because of the ease of physician programming, all of the existing tiered therapy cardiac detection systems are somewhat cumbersome in terms of how the processor inside the device actually implements the process of sorting heart rates into different zones and determining if the programmable criteria for a given zone have been satisfied. Typically, a tiered therapy detection system is implemented by having a microprocessor inside the device perform a counting or "binning" operation for each different zone, i.e., the processor determines the heart rate for a given beat and then, if the heart rate matches a given zone, a marker is stored in or added to a bin or storage location in memory that is associated with that zone. After updating the bins associated with each zone, the processor then checks each bin to see if a separate threshold criteria has been met for that zone, e.g., the processor determines if X of the last Y heart beats have occurred in the zone. It will be apparent that this approach simply requires sufficient memory to create the separate counting bins and the separate criteria for each zone and sufficient processor time to be able to update all of the bins and then check each of the bins against the criteria for each of the zones.

The primary challenge for existing tiered therapy detection systems is resolving detection issues in certain types of erratic dysrhythmias where the heart rate tends to wander across different zones (e.g., the heart rate is over 240 for only a couple of beats, then falls back to 180 for several beats, then advances to over 200 for several more beats). In this situation, it is often difficult to determine which zone is the appropriate therapy zone and when the trigger conditions for delivering therapy have been satisfied for that zone. It is also possible to have an arrhythmia which should be treated aggressively, but which avoids being classified because the trigger conditions, such as the last beat being in that zone, are never quite satisfied for a given zone. In this situation, potentially life-saving therapy might be delayed because of the inability of the therapy detection system to resolve the trigger conditions between different zones. In addition, most tiered therapy detection systems of this type have zone counter reset rules which will reset a zone counter if, for example, four consecutive beats have been detected in a lower zone. To avoid undercounting of beats in a zone, some tiered therapy also utilize an overcounting of lower zones by counting beats occurring in a higher zone as also occurring in a lower zone. Finally, if an arrhythmia terminates spontaneously in that a normal heart beat rate is detected for two or more beats, it is important that the reset conditions for each zone are handled appropriately in the event of a termination of the dysrhythmia. Obviously, there are a myriad of possible interactions and combinations of trigger, reset, overcounting and termination conditions which must be accounted for in implementing a successful and reliable tiered cardiac detection system that utilizes the classic technique of multiple zone binning as described above. For a more detailed explanation of the classic multiple zone binning technique and the potential problems in tachyarrhythmia detection, reference is made to Bach, S. et al., "Tachyarrhythmia Detection," *Implantable Cardioverter Defibrillator Therapy: The Engineering Clinical Interface*, Chpt. 15, pp. 303-323, eds. Kroll, M. and Lehmann, M. (1996), and Olson, "Safety Margins for Sensing and Detection: Programming Tradeoffs," Id., Chpt. 19, pp. 389-420.

While the existing approach to implementing a tiered therapy cardiac detection system provide very methodical and satisfactory results in terms of useful and reliable detection software for most cardiac dysrhythmias, the programming and processing required by these implementation could be improved and simplified. Additionally, the manner in which tiered therapy cardiac detection systems handle trigger, reset, overcounting and termination conditions could also be improved and simplified. Accordingly, a tiered therapy cardiac detection system which could be implemented more efficiently would provide benefits in terms of quicker response times, more accurate handling of ending, overcounting and reset conditions and reduced power consumption by the microprocessor of an implantable medical device.

SUMMARY OF THE INVENTION

The present invention provides a tiered therapy cardiac detection system for a medical device which can sense cardiac signals representative of beat-to-beat intervals and deliver at least one therapy in response to a detected cardiac dysrhythmia corresponding to one of a plurality of programmed zones of heart rates. The detection system includes a global counter that counts at least all beat-to-beat intervals indicating a heart rate greater than a programmed threshold value representative of a minimum heart rate for delivering any therapy once an initial threshold condition for detection has been satisfied. A plurality of window memories and parameter memories are provided in the device. Each window memory corresponds to a given one of the zones and stores an indication of at least whether each of a last N cardiac signals are within that zone. Each parameter memory corresponds to a given one of the zones and stores a programmed trigger value of the global counter required in order for a therapy in that zone to be delivered. Processing circuitry evaluates the global counter, the window memories and the parameter memories on a beat-by-beat basis and indicates that a cardiac dysrhythmia has been detected for a given zone if the global counter exceeds the programmed trigger value for that zone and the indications stored by the window memory for that zone satisfy a predetermined criteria.

BRIEF DESCRIPTION OF THE DRAWINGS

FIG. 8 is a schematic representation showing the effect of the global counter with a duration that is separately programmable for each zone.

FIG. 9 is a schematic representation showing the fast response of the global counter when the rhythm degenerates from VT to VF.

FIG. 10 is a schematic representation showing how three out of four slow beats will reset the detection.

FIG. 11 is a schematic representation showing the last beat in zone, 3 out 4 beats in the same zone and the average of the last four vv-intervals in the same zone, in which case, the therapy in that zone will be delivered.

FIG. 12 is a schematic representation showing when the duration limit is reached, if there are 3 out 4 of beats in a zone, then the therapy in that zone will be delivered.

FIG. 13 is a schematic representation showing when the duration limit is reached, if there is no majority in a zone then the four beat average will be used in deciding therapy.

DESCRIPTION OF THE PREFERRED EMBODIMENT

Figure 1:
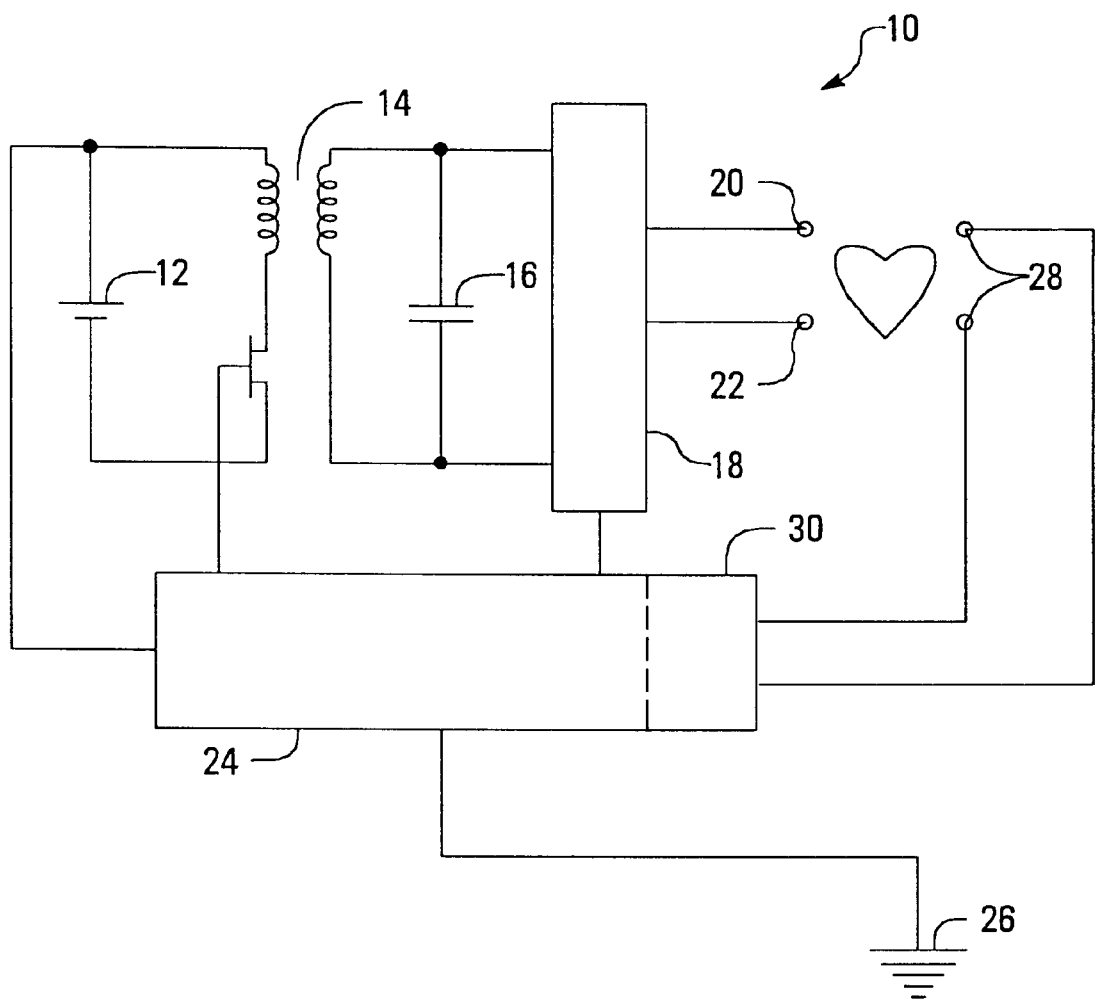
FIG. 1 is a simplified circuit diagram of an implantable cardioverter defibrillator (ICD) system.

Referring now to FIG. 1, a simplified circuit diagram of an implantable cardioverter defibrillator (ICD) system 10 in accordance with a preferred embodiment of the present invention is shown. ICD system 10 includes a battery system 12 connected to a high voltage transformer 14 for developing a high voltage across transformer 14 which is then applied to a capacitor system 16. The high voltage capacitor system 16 stores an electrical charge which is then selectively discharged through an output switching network 18 into electrodes 20, 22 as an electrical countershock for treating cardiac dysrhythmias. A control system 24, preferably a microcontroller or microprocessor with appropriate software and memory, is connected to the battery system 12, high voltage transformer 14 and output switching network 18 to control the charging and discharging of the electrical countershock. Control system 24 preferably includes telecommunication circuitry 26 for communicating external to the patient in which ICD system 10 is implanted, as well as sensing electrodes 28 and the sensing and detection circuitry 30 for detecting a cardiac dysrhythmia which is the subject of the present invention. It will be understood that the details and construction of ICD system 10 may be understood by reference to known ICD systems, such as described in U.S. Pat. No. 5,405,363 or ICD systems which are commercially available. While the present invention is presented in terms of its application to a therapy delivery system which is described as an ICD system 10, it should be understood that the present invention is applicable to any medical device which senses cardiac signals for the purpose of detecting cardiac dysrhythmias and produces a therapy to be delivered in response to the detection of a cardiac dysrhythmia, including pacemakers, anti-tachycardia pacemakers, cardioverters, atrial defibrillators and external defibrillators.

Figure 2:
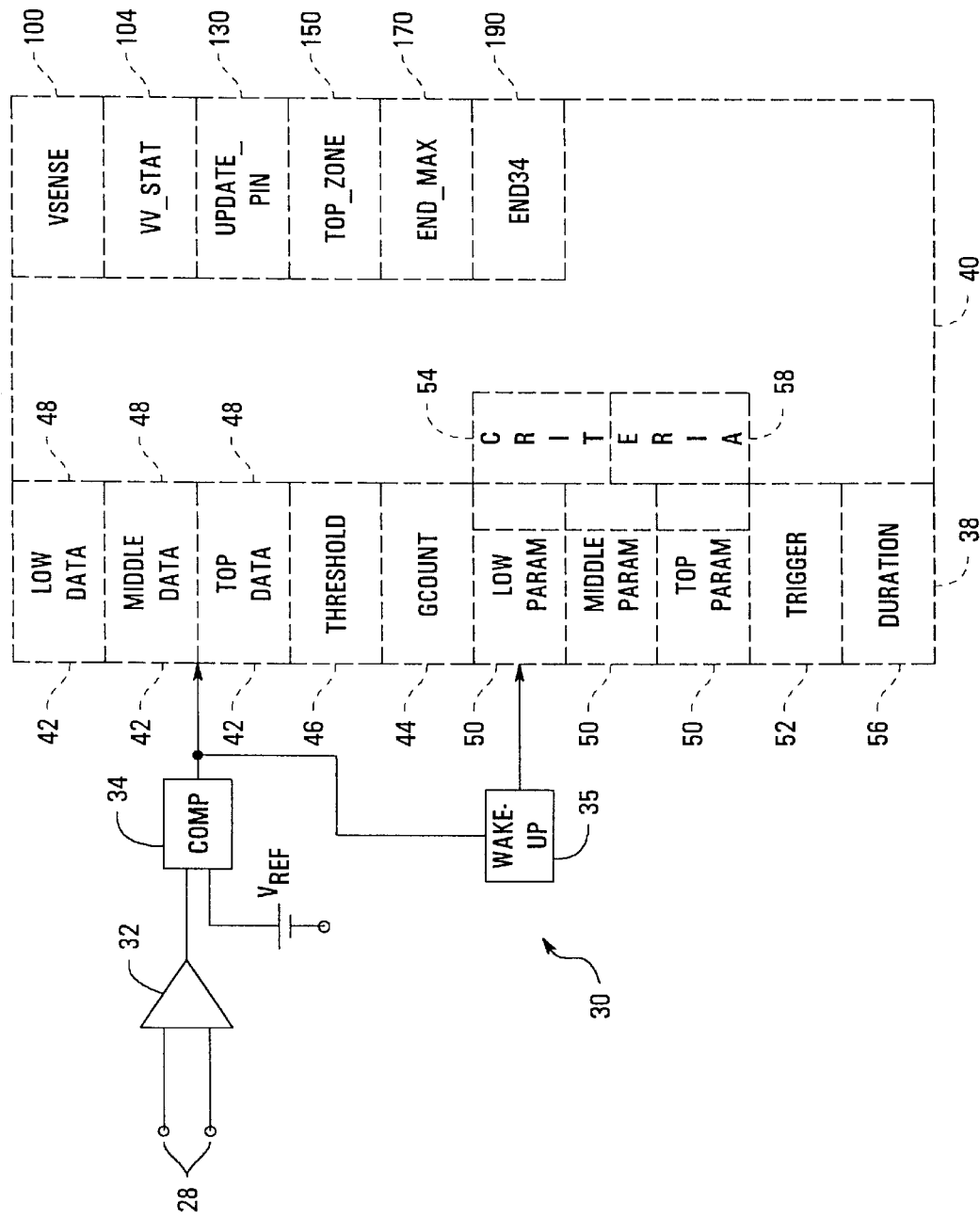
FIG. 2 is a simplified circuit diagram of a preferred embodiment of the sensing and detection circuitry of the present invention.

Referring now to FIG. 2, a simplified circuit diagram of the sensing and detection circuitry 30 is shown. Typically, very weak cardiac signals are detected across the electrodes 28 which are electrically connected to an amplifier circuit 32 which amplifies the cardiac signals and which may also filter the cardiac signals. Preferably, the output of amplifier circuit 32 is then processed by a comparator circuit 34 to detect the occurrence of each R-wave in the cardiac signal which is representative of a ventricular contraction or heart beat. The output of comparator circuit 34 is sent to detection circuitry 36 and, in a preferred embodiment to wakeup circuit 35. In the case of the preferred embodiment, detection circuitry 36 is implemented in the data memory 38 and software 40 of a microprocessor, preferably the same microprocessor which serves as the control system 18. Consequently, in order to conserve the power consumed by this microprocessor, a wakeup circuit 35 is implemented to determine the various conditions under which the microprocessor should be powered up, one of those conditions being satisfied if a predetermined initial threshold condition has been met.

In the preferred embodiment of the detection circuitry 36, data memory 38 has been programmed with a plurality of programmed zones 42 of heart rates using communication circuitry 26 which will form the boundaries for the multiple heart rate zones which the detection circuitry 36 will evaluate. Alternatively, the plurality of programmed heart rate zones 42 may be coded into data memory 38 or may be updated automatically by control system 24 in response to detected changes in the patient. While the preferred embodiment of the invention is described in terms of three heart rate zones, it will be understood that two, three, four or more zones could be used.

Typically, detection circuitry 36 times the intervals between successive R-waves to generate a series of data values referred to as the R—R intervals. These R—R intervals are measured in terms of milliseconds and reflect the beat-to-beat intervals that make up the instantaneous heart rate that is being detected at the electrodes 28. It is these R—R intervals which form the basis on which detection circuitry 36 evaluates the cardiac signals to determine whether a cardiac dysrhythmia may be present. Alternatively, cardiac signals other than R—R intervals could be used, such as P-waves or the entire QRS complex. Although the present invention is presented in terms of cardiac signals derived from the detected electrical activity of the heart, it should be understood that the present invention is equally applicable to detection systems based on other types of derived cardiac signals sensed in terms of mechanical, sonar or chemical sensors.

It should also be noted that confusion between the use of heart rate and R—R intervals to describe cardiac activity is common because these two values are inversely related to each other. In other words, as heart rate increases the R—R interval decreases. Thus, a normal sinus rhythm heart rate of 90 beats per minute (bpm) corresponds to an R—R interval of 667 milliseconds (ms), whereas a ventricular fibrillation rate of 220 bpm would correspond to an R—R interval of 273 ms. Consequently, while the present invention is expressed in terms of heart rates greater than a given value, the implementation in the preferred embodiment is actually in terms of R—R intervals less than or equal to a given value.

In accordance with the preferred embodiment of the present invention, a tiered therapy cardiac detection system 36 includes a global counter 44 defined in data memory 38 that counts at least all beat-to-beat intervals indicating a rate greater than a programmed threshold value 46 which is representative of a minimum heart rate for delivering any therapy once an initial threshold condition has been met. In the preferred embodiment, the initial threshold condition is the occurrence of three consecutive R—R intervals detected at rate above a programmed threshold value 46. Preferably, the wakeup circuit 35 implements this initial threshold condition and is set to automatically power up the microprocessor in the event that the initial threshold condition is satisfied. Alternatively, the microprocessor in the preferred embodiment of the detection circuitry 36 could be powered up on every detection R-wave to determine if the initial threshold condition is satisfied. It will be understood that while the preferred embodiment of the initial threshold condition is a given number of consecutive heart beats above the programmed threshold value 46, any number of criteria could be used for this initial threshold condition such as one single heart beat above the programmed threshold value, N heart beats above a fixed and non-programmable threshold value, X of Y heart beats above a threshold value, satisfaction of some function derived from the cardiac signal, or even a trigger provided by a sensor that did not sense electrical cardiac signals.

In the preferred embodiment, the global counter 44 is incremented once the initial threshold condition is satisfied for each R—R intervals which is above the programmed threshold value 46. In the case of an initial threshold condition which is three consecutive R—R intervals above the programmed threshold value 46, the global counter would be set to 3 at the time that the microprocessor is powered up, indicating that the 3 consecutive fast beats which were detected to satisfy the initial threshold criteria. Alternatively, it would be possible to implement the present invention such that all R—R intervals are counted by the global counter 44 once the initial threshold condition is satisfied, regardless of whether they were or were not greater than the programmed threshold value 46. In this implementation, it should be understood that even slow beats below the programmed threshold value 46 would be counted by the global counter 44 until such time as detection was reset by a reset condition or therapy was delivered.

A plurality of window memories 48 are also defined data memory 38. Each window memory corresponds to a given one of the plurality of zones 42 and stores at least an indication of whether each of a last N cardiac signals are within that programmed zone of heart rates. A plurality of parameter memories 50 are also defined in data memory 38. Each parameter memory 50 corresponds to a given one of the plurality of zones 42 and stores a programmed trigger value 52 to be compared against the global counter 44 in order for a therapy in that zone to be delivered. Preferably, the software 40 of the processing circuitry 36 evaluate the global counter 44, the window memories 48 and the parameter memories 50 on a beat-by-beat basis once the initial threshold condition has been satisfied and indicates that a cardiac dysrhythmia has been detected for a given zone 42 if the global counter 44 exceeds the programmed trigger value 52 for that zone and the indications stored by the window memory 48 for that zone satisfy certain predetermined criteria.

The predetermined criteria may either be criteria parameters 54 stored in data memory 38, threshold tests hard coded as part of the software 40, or a combination of both. In the preferred embodiment, the window memories 48 each store a bit pattern which indicates whether the last N beat-to-beat intervals are within the programmed zone of heart rates corresponding to that window memory 48 and store a rate value for each of the last N beat-to-beat intervals, preferably both of which will be compared to the criteria parameters 54 to determine whether that zone satisfies the predetermined criteria for indicating a dysrhythmia is present in that zone. In this case, the number N of last beat-to-beat intervals is preferably between 3 and 6, and optimally set at 4. Preferably, the window memories 48 store bit patterns for the latest N beat-to-beat intervals where N is between 8 and 32 and optimally is set at 8 for the two low zones and 16 for the high zone.

Preferably, the detection circuitry 36 evaluates the predetermined criteria for a zone 42 in which the global counter 44 exceeds the programmed trigger value 52 for that zone by using a set of a plurality of initial criteria, all of which must be met for the detection circuitry 36 to indicate that a cardiac dysrhythmia has been detected for that zone 52. In the preferred embodiment, the set of initial criteria include whether a last beat-to-beat interval is in the programmed zone of heart rates for that zone 42, whether a majority of the last N cardiac signals are in the programmed zone of heart rates for that zone 42, and whether an average rate of the last N cardiac signals is in the programmed zone of heart rates for that zone 42.

In the preferred embodiment, the detection circuitry 36 further includes a maximum duration parameter 56 which is compared to the global counter 44. If the maximum duration parameter 56 is exceeded, the detection circuitry 36 evaluates which of the zones 42 best fit a second predetermined criteria so as to indicate a cardiac dysrhythmia for one of the plurality of zones 42 once the maximum duration value 56 is exceeded, even though the predetermined criteria for any of the zones 42 is not met. Preferably, the second predetermined criteria is evaluated by the detection circuitry 36 using a set of a plurality of secondary criteria 58 which are applied in a hierarchical manner. As with the initial predetermined criteria, the second predetermined criteria may either be a set of secondary criteria parameters 58 stored in data memory 38, threshold tests hard coded as part of the software 40, or a combination of both. Preferably, the set of secondary criteria 58 includes determining the programmed zone of heart rates corresponding to the majority of the last N cardiac signals and, if there is no majority of the last N cardiac signals in any zone 42, determining the programmed zone of heart rates corresponding to an average of the rate values for all of the last N beat-to-beat intervals.

The detection circuitry 36 resets the global counter 44 if a predetermined number of cardiac signals are below the programmed threshold value 46. Preferably, the predetermined number of cardiac signals necessary to reset the global counter is X of Y where X is an integer in the range of 2 to 4 and Y is an integer in the range of 3 to 6. Optimally, the reset condition is satisfied by 2 out of 3 or 3 out of 4 cardiac signals being below the programmed threshold value 46. As with the initial threshold condition, however, it will be understood that there are numerous ways to implement the reset condition.

In the preferred embodiment, the present invention provides the user with the ability to program the following ranges of values for tachyarrhythmia detection and therapy zone boundaries: (1) The Rate parameter for the low zone is an R—R interval equivalent for 90 beats per minute (bpm) to 210 bpm in steps of 5 bpm (667 ms to 286 ms±10 msec). The default value is 165 bpm (364 ms). (2.) The Rate parameter for the mid zone is an R—R interval equivalent for 110 bpm to 230 bpm in steps of 5 bpm (545 ms to 261 ms±10 msec). The default value is 190 bpm (316 ms). (3.) The Rate parameter for the high zone is an R—R interval equivalent for 130 bpm to 250 bpm in steps of 5 bpm (462 ms to 240 ms±10 msec). The default value is 210 bpm (286 ms). The preferred embodiment of the present invention provides the user with the ability to program the following ranges of values for zone duration (1.) The Duration parameter for the low zone is 4 cycles to 200 cycles in steps of 2 cycles. The default value is 10 cycles (2.) The Duration parameter for the mid zone is 4 cycles to 50 cycles in steps of 2 cycles. The default value is 10 cycles. (3.) The Duration parameter for the high zone: 4 cycles to 20 cycles in steps of 2 cycles. The default value is 10 cycles.

Figure 3:
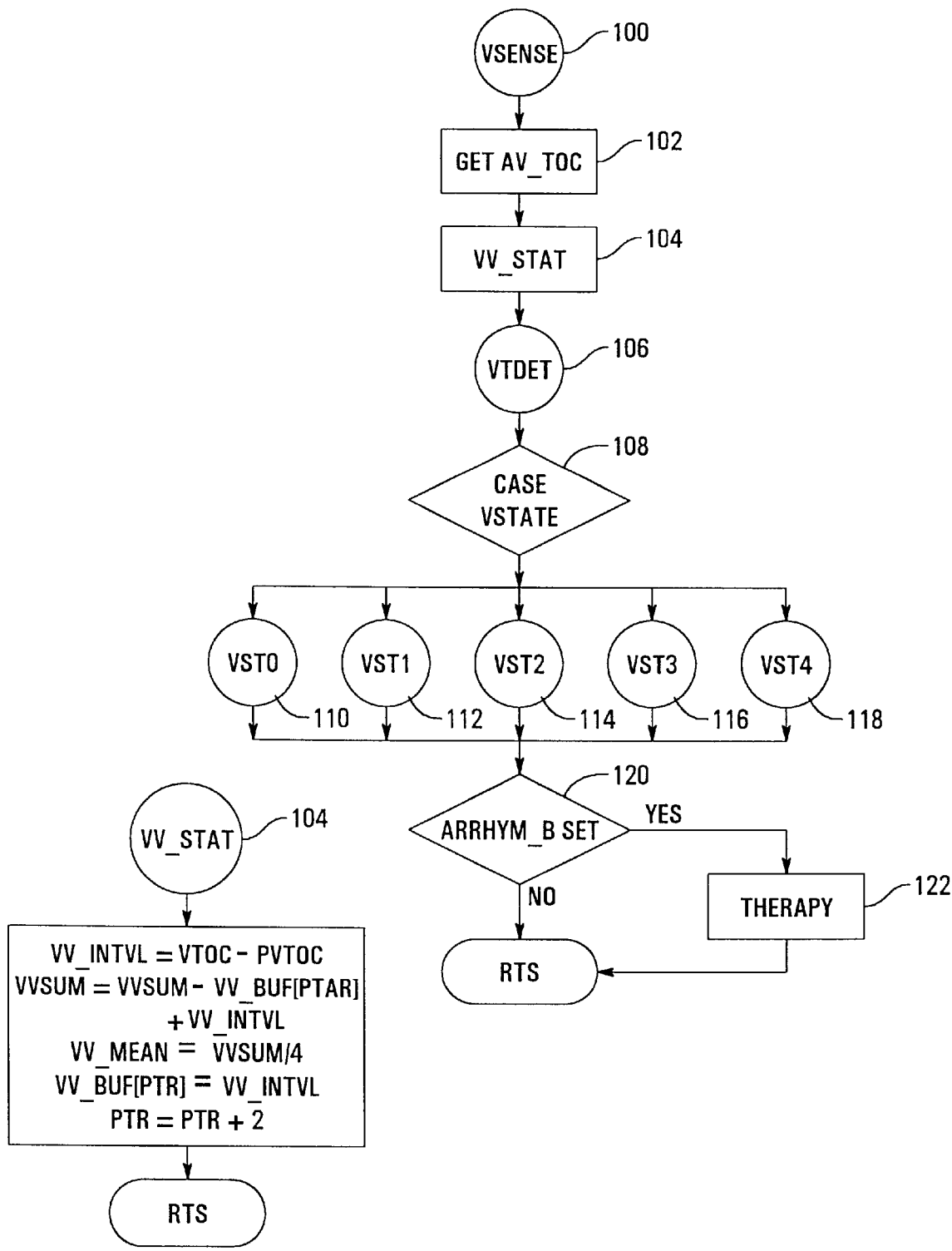
FIG. 3 is an overall flow chart of a preferred embodiment of the detection software of the present invention.

The operation of the preferred embodiment of detection circuitry 36 also can be understood by examining the following flow charts which the software 40 implements. Referring now to FIG. 3, it will be seen that in the preferred embodiment, the software 40 includes an overall VSENSE routine 100 that first obtains the most recent detected cardiac signal information at GET AV_TOC 102 which is then used to call a subroutine VV_STAT 104 which manipulates this information to produce the desired interval, sum and average information which will be used and stored by the VSENSE routine 100. Preferably, GET AV_TOC 102 obtains a 256 byte buffer representative of the latest 64 cycles of cardiac timing information obtained from the sensing circuit 34 (two bytes for each cardiac event) and including a time of clock value which establishes the time at which the signal for the cardiac event was measured. VV_STAT 104 computes an R—R interval, a running 4 beat sum of the last 4 R—R intervals and a mean over the last 4 R—R intervals. VT_STAT 104 also updates the pointer (PTR) to the current location where the indications for the current R—R interval will be stored. In the preferred embodiment, the window memories 48 include both a bit-encoded value of the recent beat pattern and a circular buffer for storing recent R—R intervals. Preferably, two bytes worth of information are stored for each beat.

At VTDET 106, the software checks the history of the current status of the detection algorithm which is represented by VSTATE 108, a working parameter which is stored in the memory. It should be understood that prior to or just after executing VTDET 106, the software may perform a check for a bradycardia condition by performing an additional software routine. If VSTATE 108 indicates a normal sinus rhythm (VSTATE=0), then VSTAT0 110 is executed. If VSTATE 108 indicates that the last one or two beats have been higher than the programmed lower rate limit 46, then VSTAT1 112 is executed. In the preferred embodiment of the software for VSTAT1 112, if a single new beat that is below the rate limit 46, then VSTATE is reset to 0, instead of using the normal 3 out of 4 reset condition previously described which is used for VSTAT2 114. If VSTATE 108 indicates that a tachycardia detection is underway, then VSTAT2 114 is executed. In the preferred embodiment, VSTATE is set to 2 once the initial threshold condition has been satisfied. Preferably, this is accomplished in the VSTAT1 112 routine once the third fast R—R interval is detected by changing VSTATE from 1 to 2. If VSTATE 108 indicates that a tachycardia condition has been identified and therapy deliver is occurring (i.e., the capacitor 16 is being charged to deliver a countershock), then VSTAT3 116 is executed. If VSTATE 108 indicates that a therapy has just been delivered and a return to normal sinus rhythm has not yet been confirmed, the VSTAT4 118 is executed. After the appropriate routine has been executed, at step 120, a flag ARRHYM_B is checked to see if a dysrhythmia has been identified which requires delivery of a therapy. If so, then the programmed therapy for the indicated dysrhythmia is delivered at step 122. If not, the VSENSE routine 100 returns until called again. It should be understood that greater or fewer subroutines may be implemented in this process, depending upon the nature and number of dysrhythmias which are encountered and the nature and number of therapies which may be delivered.

Figure 4:
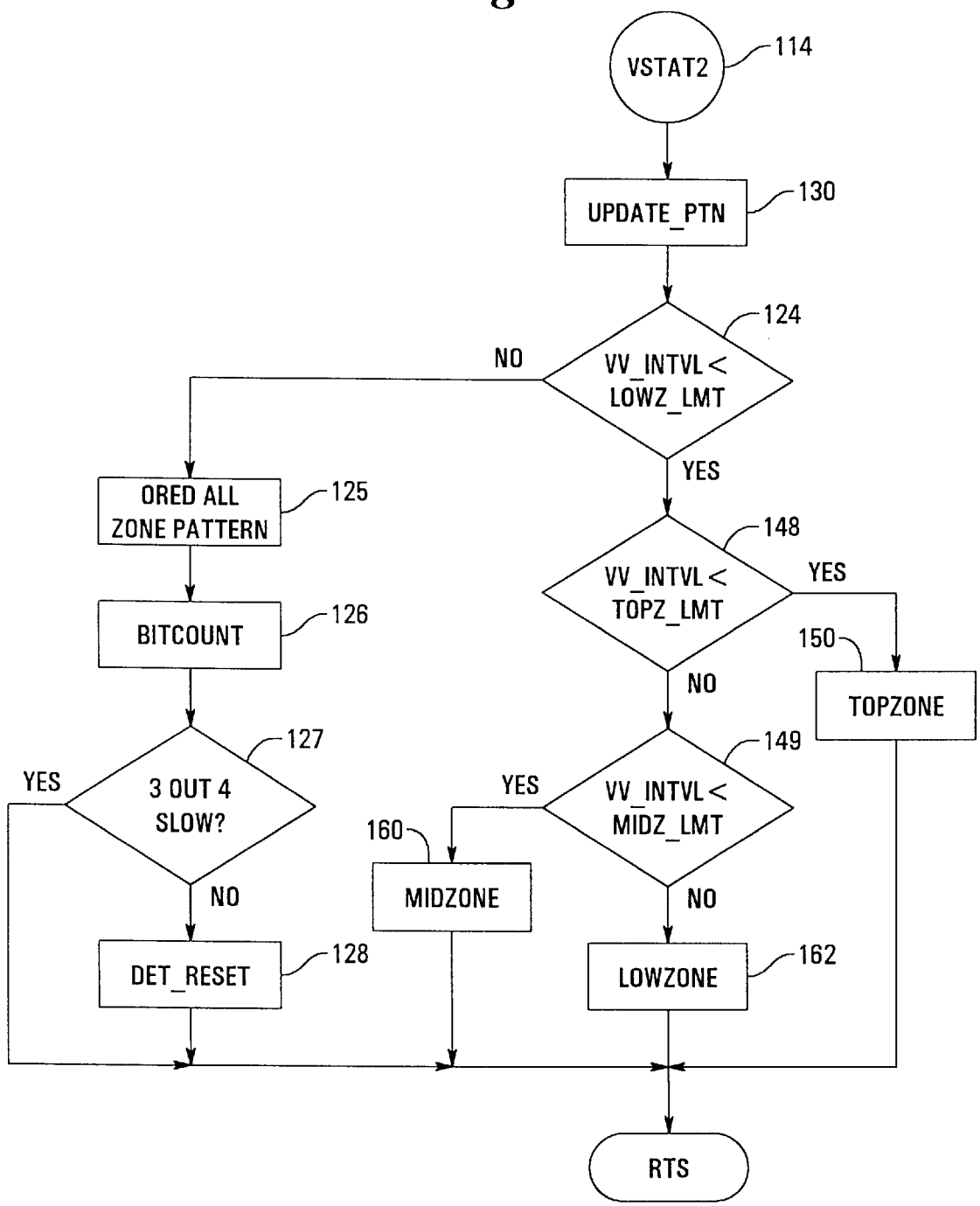
FIG. 4 is a detailed flowchart of the tachyarhythmia detection portion of the software shown in FIG. 3.

Although the preferred embodiment of the present invention may be implemented across any or all of the various VSTAT routines which may be executed, the preferred embodiment will be described with respect to VSTAT2 114. Referring now to FIG. 4, a flow chart for the preferred embodiment of the software for VSTAT2 114 is shown. At step 130, the VSTAT2 routine calls subroutine UPDATE_PTN 130 to increment the global counter 44 and update the various pointers and data values for the window memories 48. At step 124, the routine checks to see if the current R—R beat interval indicates a heart rate greater than the threshold value 46. If the current beat interval is not greater than the threshold value 46, then the routine determines whether the detection process should be reset. At step 125, the last four bits of all of the window memories 48 for all of the zones are ORed together to determine how many of the last 4 beats had rate values above the threshold value 46 at step 126. At step 127, a determination is made as to whether 3 of the last 4 beat intervals have been below the threshold value 46. If so, then the routine is finished. If not, then a detection reset subroutine 128 is called to reset the VSTATE based on a return to normal sinus rhythm. If the current beat interval indicates a rate above the threshold value 46 at step 124, then a test is made at step 148 to see if the current beat interval is in the top zone. If so, then the top zone routine 150 is called. If not, then a test is made at step 149 to see if the current beat interval indicates a rate in the middle zone. If so, then the middle zone routine 160 is called. If not, then the low zone routine 162 is called.

Figure 5:
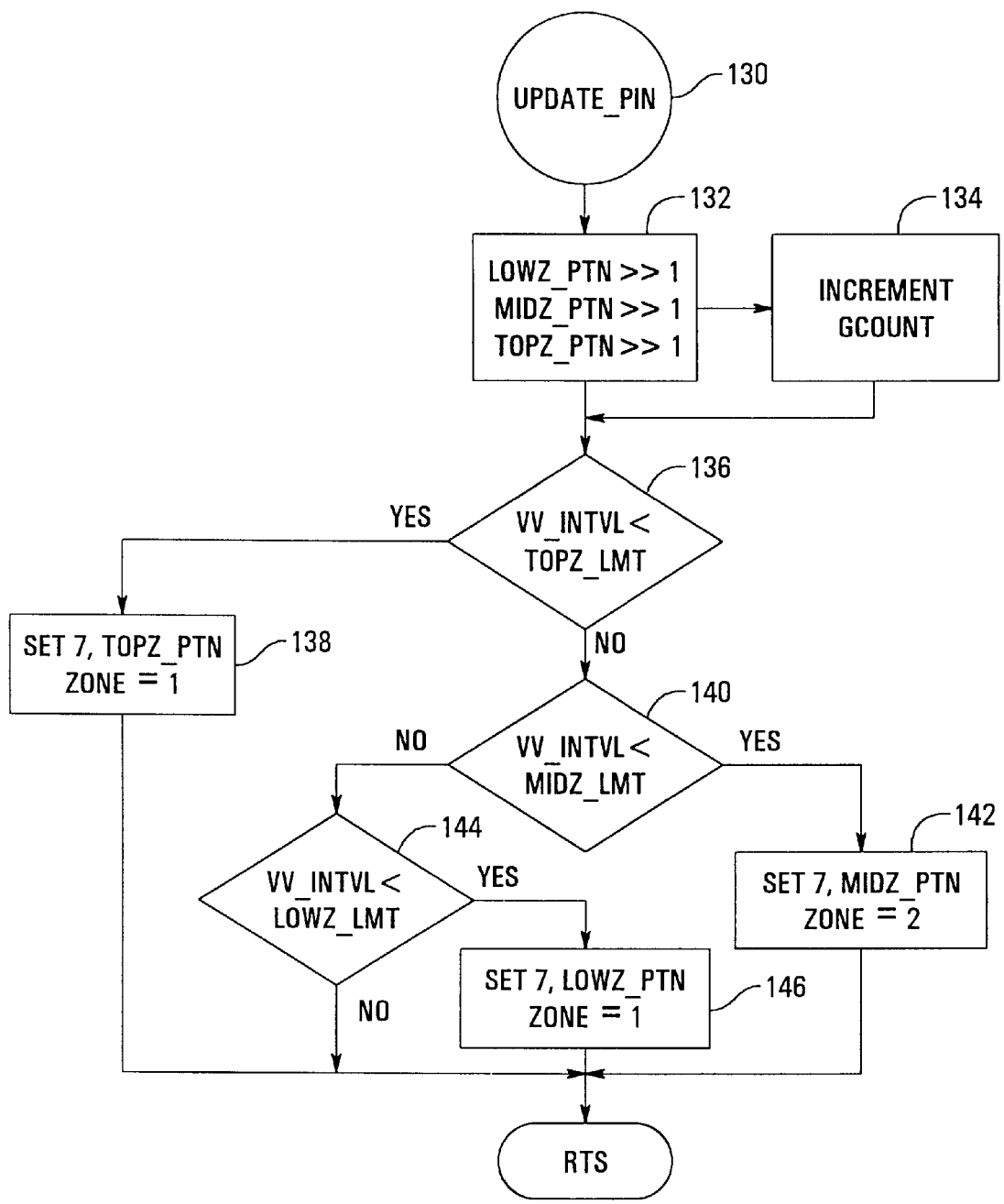
FIGS. 5–7 are detailed flowcharts showing various subroutines used by the tachyarrhythmia detection routine shown in FIG. 4.

FIG. 5 shows the details of the UPDATE_PTN routine. In this embodiment, the portion of the window memories 48 which store the bit pattern for the last eight beats are shifted right at step 132 to make room for an indication of the current R—R beat interval. The global counter 44 is incremented at step 134. Step 136 checks if the current beat interval is less than or equal to than the top zone limit (equivalent to a heart beat rate greater than or equal to the top zone limit); if so, then step 138 sets the Zone=3 (reflecting a top zone interval for the current beat) and sets the high order bit in the window memory 48 corresponding to the top zone. At step 140, a test is made on whether the current R—R interval is less than or equal to the middle zone limit; if so, then step 142 sets the Zone=2 (reflecting a middle zone interval for the current beat) and sets the high order bit in the window memory 48 corresponding to the middle zone. At step 144 step 140, a test is made on whether the current R—R interval is less than or equal to the low zone limit; if so, then step 146 sets the Zone=1 (reflecting a low zone interval for the current beat) and sets the high order bit in the window memory 48 corresponding to the low zone. Otherwise, the zone is not set and no high order bit is set, thereby indicating that the current beat interval was not above the threshold value 46.

Figure 6:
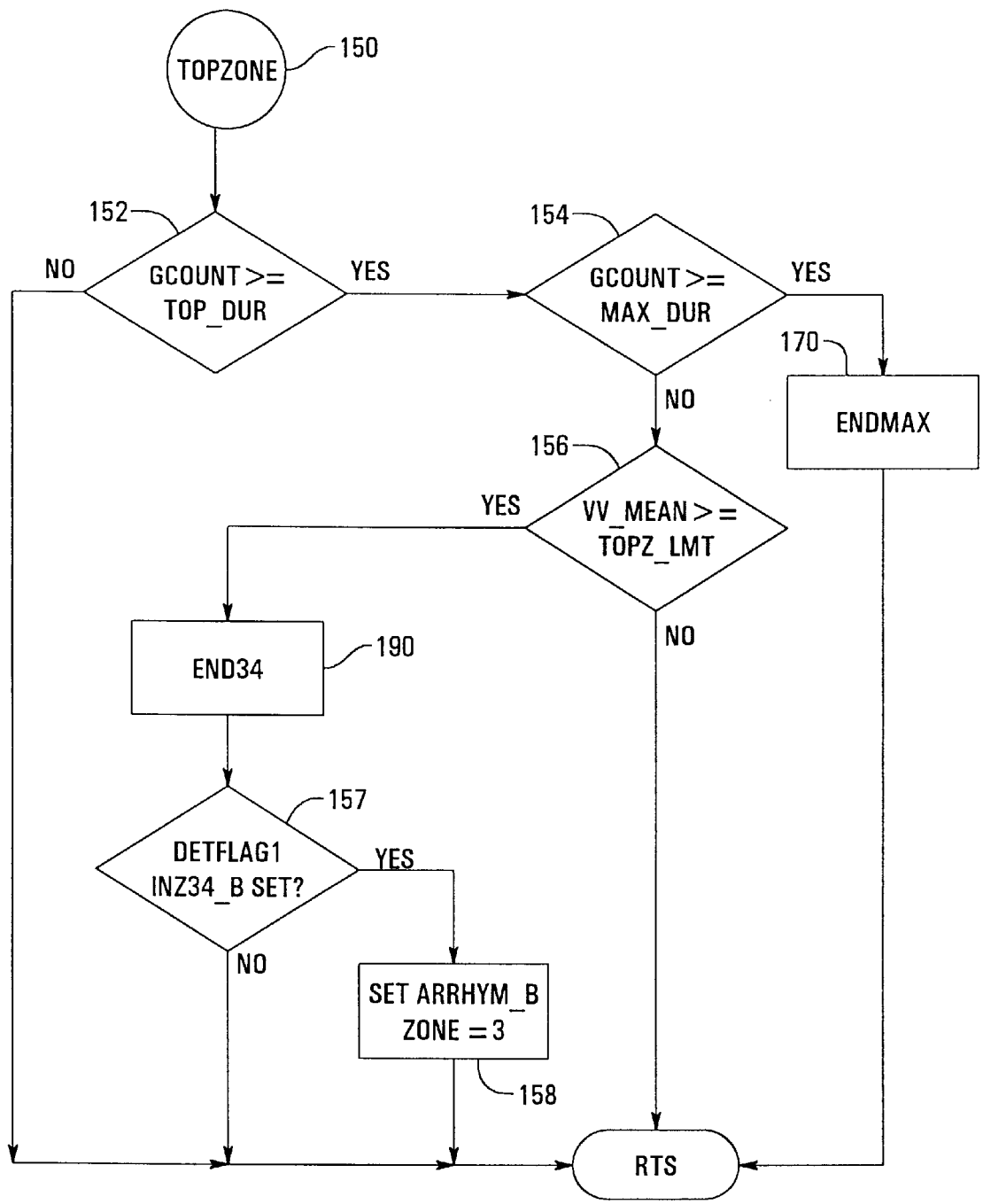

FIG. 6 shows the details of the top zone routine 150. It will be understood that the implementation of the middle zone routine 160 and bottom zone routine 162 would be similar. At step 152, a check is made to see if the global counter 44 is greater than or equal to the top zone duration as stored in the parameters 50. If not, then no further processing is done and the subroutine returns. If so, then a check is made at step 154 to see whether the global counter 44 is greater than the maximum duration value 56. If so, then the ENDMAX subroutine 170 is called. If not, then a test is made at step 156 to determine if the average rate of the last four beats is greater than the top zone average limit as stored in the parameters 50. If not, the routine returns. If the four beat average rate is greater than the top zone average limit, then the subroutine END34 190 is called to see if three of the last four beats are in the top zone. At step 157, a check is made to see if the flag for three of the last four beats in the zone is set. If so, then a flag is set indicating that there is an arrhythmia at step 158. If not, then the routine returns.

In a preferred embodiment of the top zone routine 150, an alternative detection test is applied in addition to the last, mean average test as described above once the global counter is greater than or equal to the top zone duration. In this embodiment, top zone detection shall also occur any time after top zone duration is satisfied and 12 of the last 16 intervals reflect a rate at or above the top zone rate threshold. The 12 of 16 criteria provides for the detection of undersensed or polymorphic high ventricular rates. If the top zone duration is programmed greater than sixteen, the 12 of the last 16 window shall be continuously re-evaluated until duration is met before initiating therapy delivery. When duration is met, the last beat shall be required to be in the top zone. If the last interval is not in the top zone, the window shall continue to slide until the last interval is in the top zone or detection criteria is met in another zone. It will be understood that additional tests and conditions can be implemented during the detection process, such as detection for abort conditions, presence of manual therapy delivery commands, storing of EGM and event marker information, detection of hardware or capacitor charging error conditions. The inclusion of such additional features and conditions is neither required nor precluded by operation of the present invention.

Figure 7:
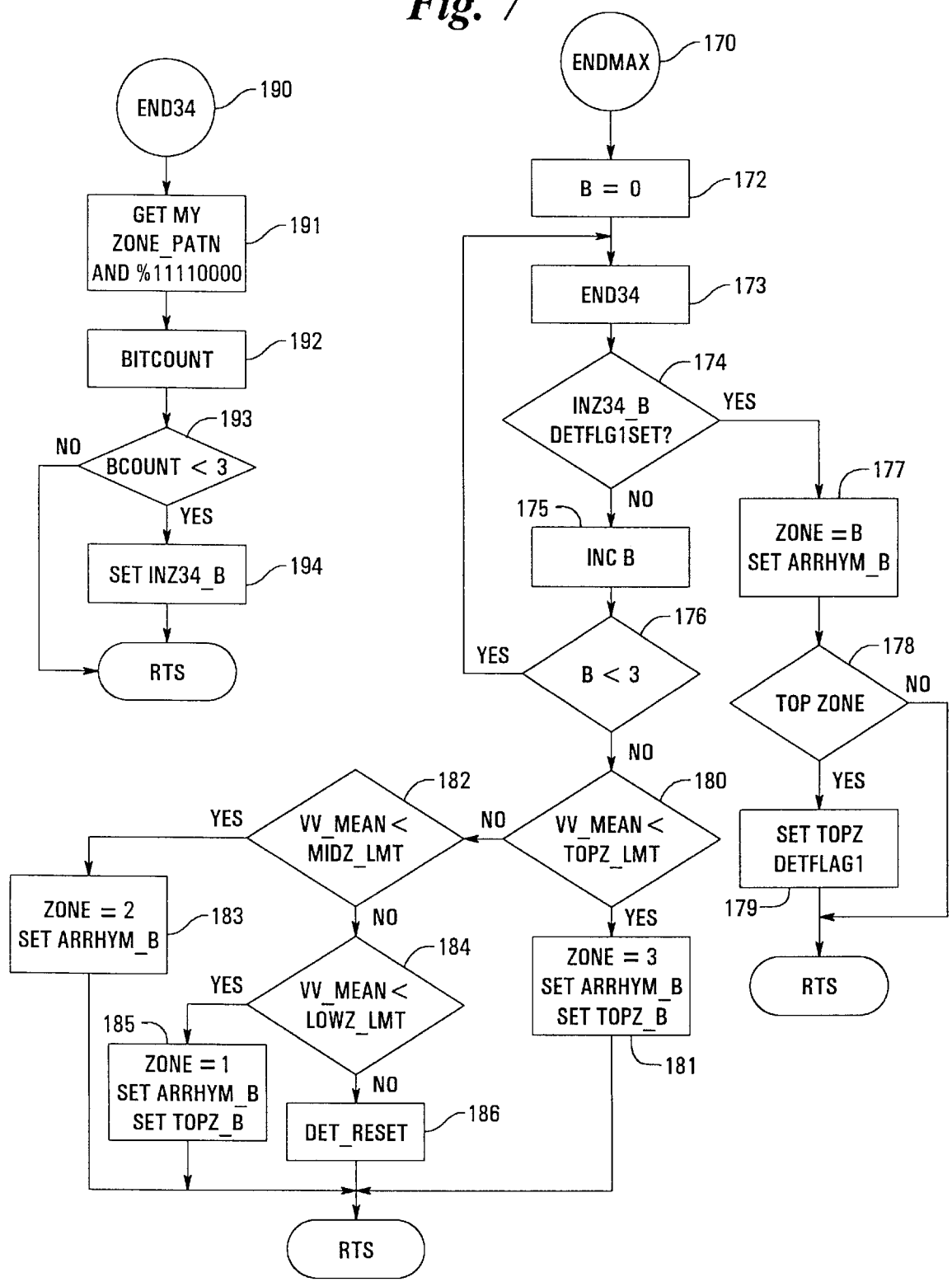

FIG. 7 shows the details of the ENDMAX subroutine 170 and the END34 subroutine 190. END 34 masks the applicable zone pattern at step 191 to get the latest 4 beat pattern only and calls a bitcount subroutine at step 192. If the value of the bit count is greater than 3 as checked at step 193, then a three of four in zone indicator is set at step 194. At the beginning of ENDMAX subroutine 170, the register B is set to zero at step 172 and a loop is setup which calls END34 190 at step 173. At step 174, a check is made to see if the three of four in the zone indicator. If not, the value of B is incremented at step 175 and the loop is repeated if B is less than three as determined at step 176. If the three of four flag is set at any point during this loop, then the arrhythmia indicator flag is set and the zone is set equal to the value B at step 177. A further check is made to see if the zone is the top zone at step 178 and, if so, another flag indicating the top zone is set at step 179 before the subroutine returns. If the maximum duration has been met, but none of the zones satisfies the test for three of the last four beats, then a check is made at step 180 to see if the average beat interval indicates a rate greater than the top zonelimit. If so, then the arrhythmia indicator flag is set and the zone is set equal to the top zone at step 181. Otherwise, a check is made at step 182 to see if the average beat interval indicates a rate greater than the middle zonelimit. If so, then the arrhythmia indicator flag is set and the zone is set equal to the middle zone at step 183. Otherwise, a check is made at step 184 to see if the average beat interval indicates a rate greater than the low zonelimit. If so, then the arrhythmia indicator flag is set and the zone is set equal to the low zone at step 185. If the average beat interval is less than the low zone average, then the DETRESET routine is called at step 186 as the arrhythmia has spontaneously returned to a normal sinus rhythm.

Referring to FIGS. 8 and 9, it will be seen that once the initial threshold condition has been met, all R—R intervals above the threshold value 46 will be counted together by the global counter 44 as fast beats, but the duration in each rate zone 42, as defined by the PRL (Primary Rate Limit), MRL (Middle Rate Limit) and TRL (Top Rate Limit), is separately programmable. For ease of programming by the physician, the PRL is typically used as the threshold value 46, although it would be possible to separate these two values. As a result, the preferred embodiment needs just one counter, the global counter 44. While it would be possible to add a second slow beat counter to determine if the reset condition were satisfied, in the preferred embodiment the bit coded pattern maintained in window memories 48 used to keep the status of the latest 8 R—R intervals also may be used to test the three out four slow beats condition for detection reset.

There are at least four reasons to use the global counting with separate programmed duration scheme of the present invention.

First, the global counting scheme of the present invention is simple in concept and predictable in its behavior when compared with the conventional multiple-zone counting scheme for a third generation ICD which implements an X out Y beats in a zone as an ad hoc added clause. Because each zone of this multiple-zone counting scheme has its own counters, it is not only necessary to deal with slow beat reset, but also with lower zone beat reset, etc. In most devices, higher zone intervals are counted as lower zone beats, but not vise versa. In some devices, these tactics coupled with X out of Y windows for each zone can create an adverse bias against the higher zone rhythms. Because of the piece-meal scholastic nature of the multiple-zone counting scheme, it is difficult to predicate when the device will finish detection and move to therapy. The trigger condition depends heavily on how the zone boundary being programmed and the heart beats wandering across zones.

Second, the meaning of the programmable parameter, per zone duration, is easy to interpret. Duration in the present invention simply means how long the physician is willing to wait, if it is known that the arrhythmia has been above PRL for such a time with the trigger criteria satisfied in the particular zone. The unit of duration for each zone can be programmed in terms of time or in number of cardiac cycles.

Third, the latest cardiac information is weighted heavier in the determination and there is a faster response to degenerating dysrhythmias. In the not uncommon dangerous case, when the patient's rhythm degenerating from VT to VF, the present invention provides a very fast trigger, enabling a quick delivery of the most appropriate therapy. For example as shown in FIG. 9, the present invention deliver a defibrillation countershock at beat 10 in total counts, even though only the latest 5 beats are in top zone. Most conventional X out of Y beats in a zone type detection systems will wait unnecessarily long in this situation and may not even deliver a defibrillation countershock, but apply anti-tachycardia pacing instead.

Fourth, there is uniform in behavior for both the initial trigger detection and the PIM (Post Intervention Monitoring). As will be shown later, the difference between initial detection in the present invention and Post Intervention Monitoring has disappeared. The only difference is the "duration" for PIM is the same for each zone, and the delay is based on the therapy. For ATP or no therapy, the post intervention delay is 4 R—R intervals. The post shock delay is programmed by the physician.

As shown in FIG. 10, in the preferred embodiment of the present invention it takes three consecutive fast beats for the tachy detection to take off (transition from VSTATE0 to VSTATE1 to VSTATE2). InVSTATE1, a single slow beat will reset the VSTATEto 0. In VSTATE2, three out of four slow beats will reset the detection to VSTATE0. It will be understood that in the preferred embodiment, a single slow beat reset in VSTATE1can be handled by the hardware of the wake up circuit 35 to conserve battery energy by not having to initiate the software detection of the present invention.

Although the fast beats are counted globally, the individual zone has their individual duration as a programmable parameter. At any beat inVSTATE2, the global tachy counter 44 can be compared with the duration parameter in the zone 42 where the current R—R interval is sensed. If the global counter 44 reaches the duration of the zone where the R—R interval is in, the following procedure will be used to decide whether and when to go to therapy. As shown in FIG. 11, when the duration limit is met in a zone, the following steps will be used to decide therapy. If the three out of four latest R—R intervals are in the same zone where duration met, and the four beat average R—R interval is also in the same zone, then the detection circuitry 36 will finish detection. The therapy regimen programmed in the zone will be used for therapy and the latest 4 beats R—R interval average will be used for coupling interval calculation. If the above three conditions were not met, the detection circuitry 36 waits for more beats, one R—R interval a time.

Any delay in the detection circuitry for the purpose of discriminating between zones must have a definite time limitation. In the cases where the beat intervals are wandering around the zones, when a programmable maximum duration delay is reached, the detection cirtcuitry 36 will will have to make a decision one zone or the other. In the preferred implementation, the programmable maximum duration delay is set equal to the longest of the zone maximum durations plus four, although it will be recognized that the programmable maximum duration delay can be independently set to any value which is greater than the longest of the zone maximum durations. As shown in FIG. 12, if there are at least three out of the latest four beats are in the same zone, the software will be set to deliver the therapy according to the regimen programmed in the zone where the majority is. The four beats R—R interval average will still be used for the coupling interval calculation, even though it may be in another zone. In this situation, it is necessary to relax the requirement that the last beat must be in the zone of therapy, when the limit of procrastination has been reached.

As shown in FIG. 13, when the maximum duration delay (in the case of the preferred embodiment, the longest zone maximum duration+4) has been reached, if the three out of four majority beats in a zone condition is not met, the detection circuitry 36 will use the 4 beats R—R interval average to decide therapy.

Having thus described the preferred embodiments of the present invention, those skilled in the art will readily appreciate the many other embodiments which can be employed within the scope of the claims provided below.

We claim:

1. A medical device having tiered therapy cardiac detection system, the medical device comprising: the detection system comprising:

a sensing system that senses cardiac signals representative of beat-to-beat intervals;

a therapy delivery system that delivers at least one therapy in response to a detected cardiac dysrhythmia corresponding to one of a plurality of programmed zones of heart rates; and a tiered therapy cardiac detection system, including a global counter that counts at least all beat-to-beat intervals indicating a rate greater than a programmed threshold value which is representative of a minimum heart rate for delivering any therapy once a predetermined initial threshold condition has been met;

a plurality of window memories, each window memory corresponding to a given one of the plurality of zones and storing at least an indication of whether each of a last N cardiac signals are within that programmed zone of heart rates;

a plurality of parameter memories, each parameter memory corresponding to a given one of the plurality of zones and storing a programmed trigger value of the global counter required in order for a therapy in that zone to be delivered; and processing circuitry that determines whether the predetermined initial threshold condition has been met and, in response, evaluates the global counter, the window memories and the parameter memories on a beat-by-beat basis and indicates that a cardiac dysrhythmia has been detected for a given zone if the global counter exceeds the programmed trigger value for that zone and the indications stored by the window memory for that zone satisfy predetermined criteria.

2. The detection system of claim 1 wherein the processing circuitry evaluates the predetermined criteria for a zone in which the global counter exceeds the programmed trigger value for that zone by using a set of a plurality of initial criteria, all of which must be met for the processing circuitry to indicate that a cardiac dysrhythmia has been detected for that zone.

3. The detection system of claim 1 further comprising a maximum duration parameter wherein the processing circuit compares the global counter with the maximum duration parameter and, if the maximum duration parameter is exceeded, evaluates which of the zones best fit a second predetermined criteria so as to indicate a cardiac dysrhythmia for one of the plurality of zones once the maximum duration value is exceeded even though the predetermined criteria for any of the zones is not met.

4. The detection system of claim 3 wherein the second predetermined criteria evaluated by the processing circuitry using a set of a plurality of secondary criteria which are applied in a hierarchical manner.

5. The detection system of claim 1 wherein the window memories store a bit pattern which indicates whether the last N beat-to-beat intervals are within the programmed zone of heart rates corresponding to that window memory, a rate value for each of the last N beat-to-beat intervals and a running average of the lest N beat-to-beat intervals.

6. The detection system of claim 5 wherein the processing circuitry evaluates the predetermined criteria for a zone in which the global counter exceeds the programmed trigger value for that zone by using a set of a plurality of initial criteria, all of which must be met for the processing circuitry to indicate that a cardiac dysrhythmia has been detected for that zone and wherein the initial criteria include: whether a last beat-to-beat interval is in the programmed zone of heart rates for that zone, whether a majority of the last N cardiac signals are in the programmed zone of heart rates for that zone, and whether an average rate of the last N cardiac signals of the last N cardiac signals is in the programmed zone of heart rates for that zone.

7. The detection system of claim 6 further comprising a maximum duration parameter wherein the processing circuit compares the global counter with the maximum duration parameter and, if the maximum duration parameter is exceeding, evaluates which of the zones best fit a second predetermined criteria so as to indicate a cardiac dysrhythmia for one of the plurality of zones once the maximum duration value is exceeded even though the predetermined criteria for any of the zones is not met.

8. The detection system of claim 7 wherein the second predetermined criteria evaluated by the processing circuitry using a set of a plurality of secondary criteria which are applied in a hierarchical manner.

9. The detection system of claim 8 wherein the set of secondary criteria evaluated by the processing circuitry includes determining the programmed zone of heart rates corresponding to the majority of the last N cardiac signals and, if there is no majority of the last N cardiac signals in any zone, determining the programmed zone of heart rates corresponding to an average of the rate values for all of the last N beat-to-beat intervals.

10. The detection system of claim 1 wherein N is in the range of 3–6.

11. The detection system of claim 1 wherein the processing circuitry resets the global counter if a predetermined number of cardiac signals have a heart rate which is below the programmed threshold value.

12. The detection system of claim 11 wherein the predetermined number of cardiac signals necessary for the processing circuitry to reset the global counter is X of Y where X is an integer in the range of 2 to 4 and Y is an integer in the range of 3 to 6.

13. The detection system of claim 1 wherein the predetermined initial threshold condition is three consecutive beat-to-beat intervals indicating a rate greater than the programmed threshold value.

14. The detection system of claim 13 wherein the processing circuitry includes a microprocessor and the detection system further comprises a circuit separate from the microprocessor that implements the predetermined threshold condition.

15. A method of implementing a tiered therapy cardiac detection system for a medical device that includes a sensing system that senses cardiac signals representative of beat-to-beat intervals, a therapy delivery system that delivers at least one therapy in response to a detected cardiac dysrhythmia corresponding to one of a plurality of programmed zones of heart rates, and a processor system and associated memory that process the cardiac signals to determine when a cardiac dysrhythmia is detected, the method comprising the processor implemented steps of:

(a) programming in the associated memory a threshold value which is representative of a minimum heart rate for delivering any therapy;

(b) defining in the associated memory a plurality of parameter memories, each parameter memory corresponding to a given one of the plurality of zones, and programming a trigger value in terms of a number of cardiac signals required in order for a therapy in that zone to be delivered;

(c) defining in the associated memory a plurality of window memories, each window memory corresponding to a given one of the plurality of zones;

(d) if aa predetermined initial threshold condition is met, on a beat-by-beat basis:

(d1) counting as a global counter at least all subsequent beat-to-beat intervals indicating a rate greater than the threshold value;

(d2) storing at least an indication of whether each of a last N cardiac signals are within that programmed zone of heart rates; and (d3) evaluating the global counter, the window memories and the parameter memories and indicating that a cardiac dysrhythmia has been detected for a given zone if the global counter exceeds the programmed trigger value for that zone and the indications stored by the window memory for that zone satisfy predetermined criteria.

16. The method of claim 15 wherein step (d3) is performed by using a set of a plurality of initial criteria, all of which must be met in order for a cardiac dysrhythmia to be indicated as detected for that zone.

17. The method of claim 15 wherein step (b) further comprising the step of programming a maximum duration parameter and wherein step (d) further comprises the step (d4) of comparing the global counter with the maximum duration parameter and, if the maximum duration parameter is exceeded, evaluating which of the zones best fits a second predetermined criteria so as to indicate a cardiac dysrhythmia for one of the plurality of zones once the maximum duration value is exceeded even though the predetermined criteria for any of the zones is not met.

18. The method of claim 17 wherein step (d4) is performed using a set of a plurality of secondary criteria which are applied in a hierarchical manner.

19. The method of claim 15 wherein step (d2) stores a bit pattern which indicates whether the last N beat-to-beat intervals are within the programmed zone of heart rates corresponding to that window memory and stores a rate value for each of the last N beat-to-beat intervals.

20. The method of claim 19 wherein step (d2) is performed by using a set of a plurality of initial criteria, all of which must be met for the processing circuitry to indicate that a cardiac dysrhythmia has been detected for that zone and wherein the initial criteria include: whether a last beat-to-beat interval is in the programmed zone of heart rates for that zone, whether a majority of the last N cardiac signals are in the programmed zone of heart rates for that zone, and whether an average rate of the last N cardiac signals of the last N cardiac signals is in the programmed zone of heart rates for that zone.

21. The method of claim 20 wherein step (b) further comprising the step of programming a maximum duration parameter and wherein step (d) further comprises the step (d4) of comparing the global counter with the maximum duration parameter and, if the maximum duration parameter is exceeded, evaluating which of the zones best fits a second predetermined criteria so as to indicate a cardiac dysrhythmia for one of the plurality of zones once the maximum duration value is exceeded even though the predetermined criteria for any of the zones is not met.

22. The method of claim 21 wherein step (d4) is performed using a set of a plurality of secondary criteria which are applied in a hierarchical manner.

23. The method of claim 22 wherein step (d4) is performed by determining the programmed zone of heart rates corresponding to the majority of the last N cardiac signals and, if there is no majority of the last N cardiac signals in any zone, determining the programmed zone of heart rates corresponding to an average of the rate values for all of the last N beat-to-beat intervals.

24. The method of claim 15 further comprising the step of (d4) of resetting the global counter if a predetermined number of cardiac signals are below the programmed threshold value.

25. The method of claim 24 wherein the predetermined number of cardiac signals necessary for the processing circuitry to reset the global counter is X of Y where X is an integer in the range of 2 to 4 and Y is an integer in the range of 3 to 6.

26. The method of claim 15 wherein the predetermined initial threshold condition is three consecutive beat-to-beat intervals indicating a rate greater than the programmed threshold value.

* * * * *